United States Patent [19]

Fuchs et al.

[11] 4,316,913
[45] Feb. 23, 1982

[54] ARTHROPODICIDALLY ACTIVE STYRYLCYCLOPROPANECARBOXYLIC ACID ESTERS

[75] Inventors: Rainer Fuchs, Wuppertal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 136,023

[22] Filed: Mar. 31, 1980

[30] Foreign Application Priority Data

Apr. 23, 1979 [DE] Fed. Rep. of Germany ....... 2916358

[51] Int. Cl.³ .................. A01N 53/00; C07C 69/743; C07C 121/75
[52] U.S. Cl. .............................. 424/304; 260/465 D; 542/429; 560/18; 560/65; 424/278; 424/282; 424/308
[58] Field of Search .................... 260/465 D, 340.5 R; 560/18, 21, 65; 562/474; 424/304, 308, 278, 282; 542/429

[56] References Cited

U.S. PATENT DOCUMENTS 4,183,942 1/1980 Engel ................................. 424/274

FOREIGN PATENT DOCUMENTS 1959401 9/1970 Fed. Rep. of Germany.
1966839 7/1974 Fed. Rep. of Germany.
2706184 8/1977 Fed. Rep. of Germany.
2738150 3/1978 Fed. Rep. of Germany.
2848495 5/1979 Fed. Rep. of Germany.
2827101 1/1980 Fed. Rep. of Germany.
2067854 8/1971 France.

Primary Examiner—Dolph H. Torrence
Attorney, Agent, or Firm—Sprung, Felfe, Horn, Lynch & Kramer

[57] ABSTRACT

Substituted styrylcyclopropanecarboxylic acid esters of the formula

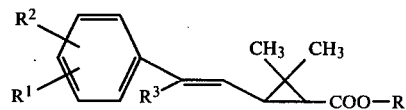

in which
R represents $C_{1-4}$-alkyl or an alcohol radical customary in pyrethroids,
$R^1$ represents alkoxy or alkylthio, either of which is optionally substituted by halogen and
$R^2$ represents hydrogen or alkoxy, or
$R^1$ and $R^2$ together represent optionally halogen-substituted alkylenedioxy, and
$R^3$ represents hydrogen or chlorine, exhibit arthropodicidal activity. A novel synthesis is shown involving reaction of

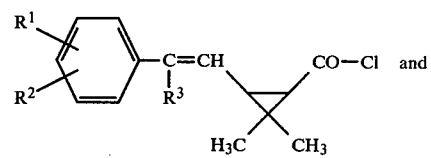

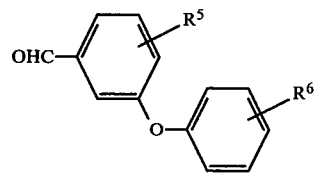

in the presence of an alkali metal cyanide to produce an end product wherein R is an α-cyano-3-phenoxybenzyl ester.

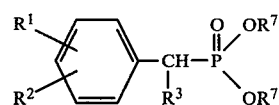

is reacted with

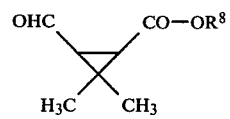

in the presence of a base to produce certain novel intermediates.

7 Claims, No Drawings

ARTHROPODICIDALLY ACTIVE STYRYLCYCLOPROPANECARBOXYLIC ACID ESTERS

The invention relates to certain new substituted styrylcyclopropanecarboxylic acid esters, to a process for their preparation and to their use as arthropodicides, especially as insecticides and acaricides. The invention also relates to certain new intermediates for use in the preparation of said esters.

It is known that certain styryl-cyclopropanecarboxylic acid phenoxybenzyl esters, for example 3-(2-phenyl-vinyl)- and 3-(2-chloro-2-phenyl-vinyl)-2,2-dimethylcyclopropanecarboxylic acid 3-phenoxy-benzyl ester, have an insecticidal and acaricidal action (see DE-OS (German Published Specification) No. 2,738,150). However, the action of these compounds is not always satisfactory, especially in the case of low concentrations of active compound and when small amounts are used.

The present invention now provides, as new compounds, the substituted styryl-cyclopropanecarboxylic acid esters of the general formula

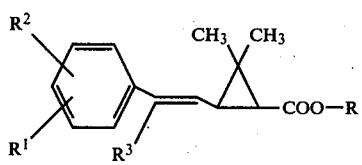

in which
R represents $C_{1-4}$-alkyl or an alcohol radical customary in pyrethroids,
$R^1$ represents alkoxy or alkylthio, either of which is optionally substituted by halogen and
$R^2$ represents hydrogen or alkoxy, or
$R^1$ and $R^2$ together represent optionally halogen-substituted alkylenedioxy, and
$R^3$ represents hydrogen or chlorine.

The general formula (I) also includes the various possible steroisomers—as well as the optically active isomers—and mixtures thereof.

The new compounds of the formula (I) are distinguished by a high insecticidal and acaricidal activity. Surprisingly, the styrylcyclopropanecarboxylic acid esters according to the invention exhibit a considerably higher insecticidal and acaricidal action than compounds known from the state of the art which are of analogous structure and have the same type of action.

The preferred styrylcyclopropanecarboxylic acid derivatives of the formula (I) are those in which
$R^1$ represents $C_1-C_4$-alkoxy, $C_1-C_4$-alkylthio, $C_1-C_2$-fluoroalkoxy, $C_1-C_2$-chlorofluoroalkoxy or $C_1-C_2$-fluoroalkylthio and
$R^2$ represents hydrogen or methoxy, or
$R^1$ and $R^2$ together represent $C_1-C_2$-alkylenedioxy or $C_1-C_2$-fluoroalkylenedioxy,
$R^3$ represents chlorine and
R represents an optionally substituted phenoxybenzyl radical of the general formula

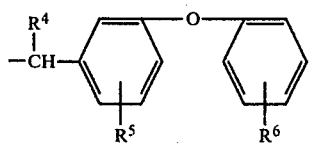

wherein
$R^4$ represents hydrogen, cyano or ethynyl and
$R^5$ and $R^6$ are identical or different and represent hydrogen or fluorine.

The invention also provides a process for the preparation of a styrylcyclopropanecarboxylic acid ester of the formula (I), in which a styrylcyclopropanecarboxylic acid of the general formula

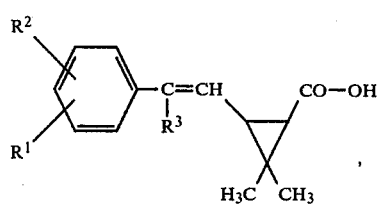

in which $R^1$, $R^2$ and $R^3$ have the meanings indicated above, or a reactive derivative thereof, is reacted with an alcohol customary in pyrethroids, or a reactive derivative thereof.

The invention also provides the styrylcyclopropanecarboxylic acids of the general formula

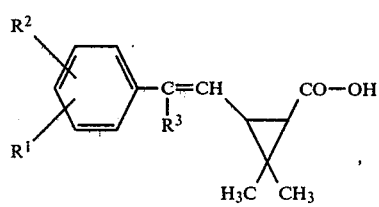

in which $R^1$, $R^2$ and $R^3$ have the meanings indicated above, and a process for the preparation of such a styrylcyclopropanecarboxylic acid of the formula (II), in which a substituted benzylphosphonic acid ester of the general formula

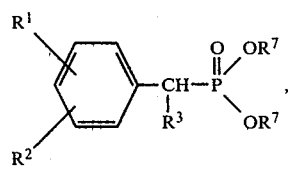

in which
$R^1$, $R^2$ and $R^3$ have the meanings indicated above, and
$R^7$ represents alkyl or phenyl, or
the two radicals $R^7$ together represent alkanediyl (alkylene)
is reacted with a formyl-cyclopropanecarboxylic acid ester of the general formula

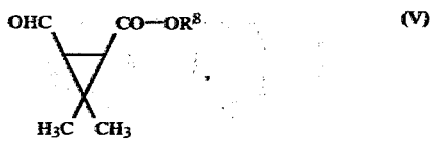

(V)

in which $R^8$ represents alkyl, in the presence of a base and if appropriate using a diluent, and the styrylcyclopropanecarboxylic acid ester of the general formula

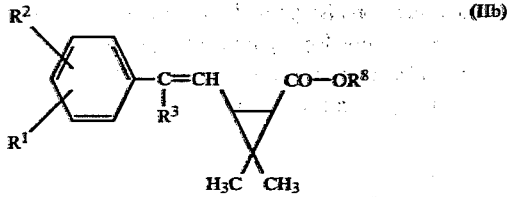

(IIb)

in which $R^8$ has the meaning indicated above, thereby formed is saponified by any known method, for example by heating with sodium hydroxide in aqueous alcohol, to give the corresponding styrylcyclopropanecarboxylic acid of the formula (II).

In a preferred process variant (a) for the preparation of a compound of the formula (I), as a reactive derivative of a styrylcyclopropanecarboxylic acid of the formula (II), the corresponding carboxylic acid chloride of the formula

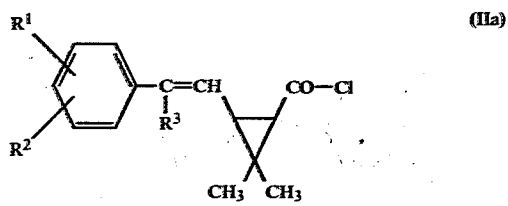

(IIa)

in which $R^1$, $R^2$ and $R^3$ have the meanings indicated above, is reacted with a phenoxybenzyl alcohol of the general formula

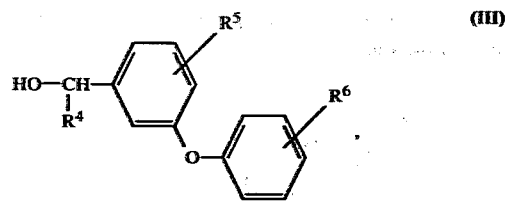

(III)

in which $R^4$, $R^5$ and $R^6$ have the meanings indicated above, in the presence of an acid acceptor and using a diluent.

A particularly preferred process variant (b) for the preparation of a compound of the formula (I) in which R represents a radical (IIIb) wherein $R^4$ represents cyano is characterized in that a carboxylic acid chloride of the formula (IIa), above, is reacted with a phenoxybenzaldehyde of the general formula

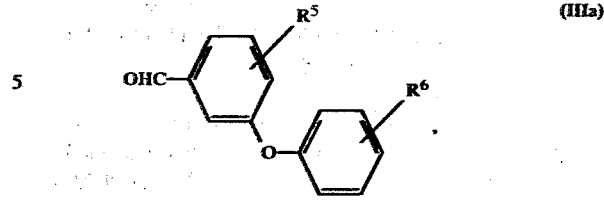

(IIIa)

in which $R^5$ and $R^6$ have the meanings indicated above, in the presence of at least an equimolar amount of an alkali metal cyanide (for example sodium cyanide or potassium cyanide) and in the presence of a catalyst, and using a diluent.

If, for example, 3-(2-chloro-2-(4-methoxy-phenyl)-vinyl)-2,2-dimethyl-cyclopropane-1-carboxylic acid chloride and 3-(3-fluoro-phenoxy)-benzyl alcohol are used as starting materials in variant (a) and 3-(2-chloro-2-(4-trifluoro-methoxy-phenyl)-vinyl)-2,2-dimethyl-cyclopropane-1-carboxylic acid chloride and 3-phenoxy-4-fluoro-benzaldehyde and sodium cyanide are used as starting materials in process variant (b), the corresponding reactions can be outlined by the following equations:

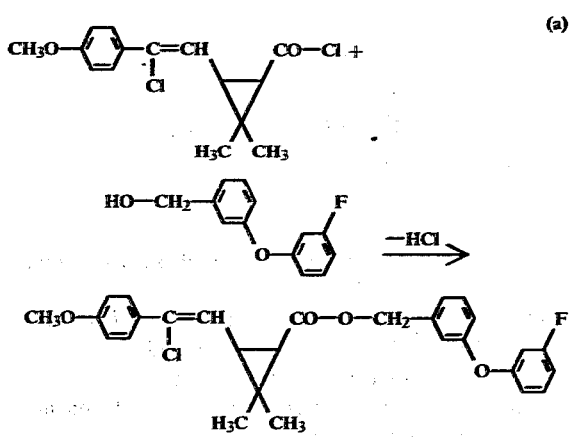

(a)

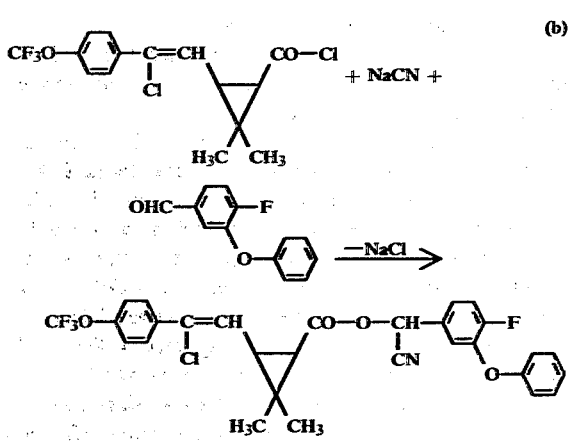

(b)

The formulae (II), (IIa), (III) and (IIIa) provide definitions of the starting materials to be used. Preferably, in these formulae, R to $R^6$ have those meanings which have already been mentioned as preferred in the case of the definition of R to $R^6$ in formula (I).

The styrylcyclopropanecarboxylic acids (II) and the corresponding acid chlorides (IIa) to be used as starting compounds are new. The carboxylic acids of the formula (II) are obtained from the corresponding alkyl esters, preferably the methyl or ethyl esters, by saponification, that is to say by heating to temperatures between 50° and 150° C. for several hours, for example with sodium hydroxide in aqueous alcohol. Working up is effected in the customary manner, for example by stripping off the alcohol in vacuo, diluting the residue with methylene chloride, drying the organic phase and stripping off the solvent.

The esters corresponding to the carboxylic acids of the formula (II) are obtained, as illustrated above, by reacting substituted benzyl-phosphonic acid esters of the formula (IV), above, with formyl-cyclopropanecarboxylic acid esters of the formula (V), above, in the presence of a base, for example sodium methylate, and if appropriate using a diluent, for example ethanol or tetrahydrofuran, at a temperature between −10° and +50° C. Working up can be carried out in the customary manner, for example by diluting the reaction mixture with water, extracting the mixture with methylene chloride, drying the organic phase, stripping off the solvent and distilling the product which remains, in vacuo. The acid chlorides of the formula (IIa) corresponding to the carboxylic acids of the formula (II) can be prepared by reacting the carboxylic acids (II) with a halogenating agent, for example thionyl chloride, if appropriate using a diluent, for example carbon tetrachloride, at a temperature between 10° and 100° C. and they can be purified by vacuum distillation.

Examples of the carboxylic acids of the formula (II) and of the corresponding acid chlorides (IIa) and esters which may be mentioned are: 3-(2-chloro-2-(4-methoxy-phenyl)-vinyl-, 3-(2-chloro-2-(4-ethoxy-phenyl)-vinyl-, 3-(2-chloro-2-(3,4-dimethoxy-phenyl)-vinyl-, 3-(2-chloro-2-(4-methylthio-phenyl)-vinyl-, 3-(2-chloro-2-(3,4-methylene-dioxy-phenyl)-vinyl-, 3-(2-chloro-2-(4-trifluoromethoxy-phenyl)-vinyl-, 3-(2-chloro-2-(4-chlorodifluoromethoxy-phenyl)-vinyl-, 3-(2-chloro-2-(4-(1,1,2,2-tetrafluoroethoxy-phenyl)-vinyl-, 3-(2-chloro-2-(4-(2-chloro-1,1,2-trifluoro-ethoxy)-phenyl)-vinyl-, 3-(2-chloro-2-(4-trifluoromethylthio-phenyl)-vinyl-, 3-(2-chloro-2-(3,4-difluoromethylene-dioxy-phenyl)-vinyl- and 3-(2-chloro-2-(3,4-trifluoro-ethylenedioxy-phenyl)-vinyl-2,2-dimethylcyclopropanecarboxylic acid and the corresponding acid chlorides, methyl esters and ethyl esters.

Formula (IV) provides a definition of the substituted benzylphosphonic acid esters to be used as intermediate products. Preferably, in this formula, $R^1$, $R^2$ and $R^3$ have those meanings which are mentioned as preferred in the case of the definition of $R^1$, $R^2$ and $R^3$ in formula (I) and $R^7$ preferably represents methyl, ethyl or phenyl, or both the radicals $R^7$ together represent 2,2-dimethyl-propane-1,3-diyl.

Examples of these intermediate products which may be mentioned are: 4-methoxy-, 4-ethoxy-, 3,4-dimethoxy-, 4-methylthio-, 3,4-methylenedioxy-, 4-trifluoromethoxy-, 4-chlorodifluoromethoxy-, 4-(1,1,2,2-tetrafluoroethoxy)-, 4-(2-chloro-1,1,2-trifluoro-ethoxy)-, 4-trifluoromethylthio-, 3,4-difluoromethylenedioxy- and 3,4-trifluoroethylenedioxy-α-chloro-benzyl-phosphonic acid dimethyl ester, -α-chloro-benzyl-phosphonic acid diethyl ester and -α-chloro-benzyl-phosphonic acid diphenyl ester.

The benzylphosphonic acid esters of the formula (IV) which are unsubstituted in the α-position, are known and they can be prepared by known processes.

The benzylphosphonic acid esters of the formula (IV) which are substituted by Cl in the α-position have not hitherto been described in the literature. They are obtained by reacting α-hydroxy-benzylphosphonic acid esters of the general formula

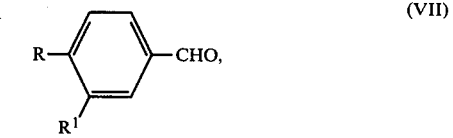

in which $R^1$, $R^2$ and $R^7$ have the meanings indicated above, with chlorinating agents, for example thionyl chloride, at a temperature between 0° and 100° C., if appropriate in the presence of a basic catalyst, for example pyridine, and if appropriate using a diluent, for example methylene chloride (see, for example, Chimia 28 (1974), 656–657; and J. Am. Chem. Soc. 87 (1965), 2777–2778).

Formula (VI) provides a definition of the α-hydroxy-benzylphosphonic acid esters which can be used as intermediate products. Preferably, in this formula, $R^1$, $R^2$ and $R^7$ have those meanings which are mentioned as preferred in the case of the definition of $R^1$ and $R^2$ in formula (I) and of $R^7$ in formula (IV).

Examples of these intermediate products which may be mentioned are: 4-methoxy-, 4-ethoxy-, 3,4-dimethoxy-, 4-methylthio-, 3,4-methylenedioxy-, 4-trifluoromethoxy-, 4-chlorodifluoromethoxy-, 4-(1,1,2,2-tetrafluoro-ethoxy)-, 4-(2-chloro-1,1,2-trifluoro-ethoxy)-, 4-trifluoromethylthio-, 3,4-difluoromethylenedioxy- and 3,4-trifluoroethylenedioxy-α-hydroxy-benzyl-phosphonic acid dimethyl ester, -α-hydroxy-benzyl-phosphonic acid diethyl ester and -α-hydroxybenzyl-phosphonic acid diphenyl ester.

The α-hydroxy-benzylphosphonic acid esters of the formula (VI) are new compounds. They are obtained by processes which are known in principle, in general by reacting aldehydes of the general formula

in which R and $R^1$ have the meanings indicated above, with phosphorous acid esters of the general formula $$H-P\begin{matrix}O\\\phantom{.}\end{matrix}\begin{matrix}OR^7\\OR^7\end{matrix} \quad (VIII)$$

wherein $R^7$ has the meaning indicated above, if appropriate in the presence of a catalyst, for example triethylamine, at a temperature between 0° and 150° C., preferably at 20° to 100° C. (see Houben-Weyl, Methoden der organischen Chemie (Methods of Organic Chemistry), 4th. edition (1963), volume 12/1, pages 475–483, Georg Thieme Verlag, Stuttgart).

Examples of the aldehydes of the formula (VII) which may be mentioned are: 4-methoxy-, 4-ethoxy-, 3,4-dimethoxy-, 4-methylthio-, 3,4-methylenedioxy-, 4-trifluoromethoxy-, 4-chlorodifluoromethoxy-, 4-(1,1,2,2-tetrafluoroethoxy)-, 4-(2-chloro-1,1,2-trifluoroethoxy)-, 4-trifluoromethylthio-, 3,4-difluoromethylenedioxy- and 3,4-trifluoroethylenedioxy-benzaldehyde.

Aldehydes of the formula (VII) are known, (see for example, J. Gen. Chem. USSR 30 (1960), 3103; Bull. Soc. Chim. France 1955, 1594; ibid. 1962, 254–262; J. Org. Chem. 37 (1972), 673; DE-OS (German Published Specification) No. 2,029,556; U.S. Pat. No. 3,387,037; and J. Med. Chem. 16 (1973), 1399).

Examples of the phosphorous acid esters of the formula (VIII) which may be mentioned are: phosphorous dimethyl ester (dimethyl phosphite), phosphorous diethyl ester (diethyl phosphite) and phosphorous diphenyl ester (diphenyl phosphite).

The phosphorous acid esters of the formula (VIII) are known compounds.

Formula (V) provides a definition of the formyl-cyclopropane-carboxylic acid esters also to be used as intermediate products. Preferably, in this formula, $R^8$ represents straight-chain or branched alkyl with 1 to 4, especially 1 or 2, carbon atoms.

Specific examples of the compounds of the formula (V) which may be mentioned are: 2,2-dimethyl-3-formyl-cyclo-propane-1-carboxylic acid methyl ester and ethyl ester.

The compounds of the formula (V) are known and they can be prepared by known processes, in general by reacting known alken-1-yl-cyclopropanecarboxylic acid esters with ozone (see, for example, U.S. Pat. No. 3,679,667).

Preferred alcohols and aldehydes for the preparation of the compounds of the formula (I) are: 3-phenoxy-, 3-(3-fluorophenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-benzyl alcohol, 3-phenoxy-, 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-α-cyano-benzyl alcohol, 3-phenoxy-, 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluoro-α-ethynyl-benzyl alcohol and 3-phenoxy-, 3-(3-fluoro-phenoxy)-, 3-(4-fluoro-phenoxy)-, 3-phenoxy-4-fluoro-, 3-(3-fluoro-phenoxy)-4-fluoro- and 3-(4-fluoro-phenoxy)-4-fluorobenzaldehyde.

The process for the preparation of the styrylcyclopropanecarboxylic acid esters according to the invention is preferably carried out using a suitable solvent or diluent. Possible solvents or diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane, ketones, such as acetone, methyl ethyl ketone, methyl isopropyl ketone and methyl isobutyl ketone; and nitriles, such as acetonitrile and propionitrile.

When the reaction is carried out in a two-phase medium, water is used as the second solvent component.

In the process described as particularly preferred, using an acid chloride of the formula (IIa) and a phenoxy-benzyl alcohol of the formula (III) as starting materials, any of the customary acid-binding agents can be used as an acid acceptor. Alkali metal carbonates and alcoholates, such as sodium carbonate and potassium carbonate, sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly suitable.

In the process described as particularly preferred, using an acid chloride of the formula (IIa) and a phenoxy-benzaldehyde of the formula (IIIa) as starting materials, a compound which usually serves as an auxiliary for the phase transfer of reactants in the case of reactions in multiphase media is in general used as a catalyst. Tetra-alkyl- and trialkyl-aralkyl-ammonium salts, for example, tetrabutyl-ammonium bromide and trimethyl-benzyl-ammonium chloride, may be mentioned in particular.

The reaction temperature can be varied within a substantial range. In general, the reaction is carried out at from 0° to 100° C., preferably at 10° to 50° C. The process according to the invention is in general carried out under normal pressure.

The starting materials are usually employed in equimolar amounts for carrying out the process according to the invention. An excess of one or the other of the reaction components brings no substantial advantages. The reaction is in general carried out in one or more diluents in the presence of an acid acceptor or of a catalyst, and the reaction mixture is stirred at the required temperature for several hours. The reaction mixture is then shaken with toluene/water and the organic phase is separated off, washed with water and dried. After distilling off the solvent in vacuo, the product is in general obtained in the form of an oil; some of these oils cannot be distilled without decomposition, but can be freed from the last volatile constituents by so-called "incipient distillation", that is to say by prolonged heating to moderately elevated temperatures under reduced pressure, and can be purified in this manner. The refractive index is used for their characterization.

As already mentioned, the new styryl-cyclopropane-carboxylic acid esters are distinguished by a high insecticidal and acaricidal activity.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp.,

*Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothios spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates, as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides arthropodicidal compositions containing as active ingredient a compound of the present invention in admixture with a solid or liquefied gaseous diluent or carrier or in admixture with a liquid diluent or carrier containing a surface-active agent.

The present invention also provides a method of combating arthropods (especially insects and acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The intermediates for preparing the novel end compounds could be prepared, for example, as follows:

EXAMPLE 1

(a)

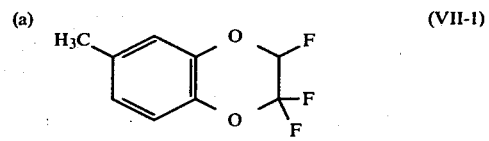

(VII-1)

124 g of 4-methylpyrocatechol were initially introduced, together with 110 g of potassium hydroxide, into 300 ml of tetramethylenesulphone at 110° C. 170 g of trifluorochloroethylene were then passed in over a period of 4 hours. The batch was subsequently distilled over a column under 15 mm Hg, distillate being removed up to a passing-over temperature of 85° C. After separating off the aqueous phase in the receiver, the product was distilled again. 133 g (65% of theory) of 6-methyl-2,2,3-trifluoro-1,4-benzodioxene were obtained at a boiling point of 70°–72° C./12 mm Hg ($n_D^{20}$: 1.4565).

(b)

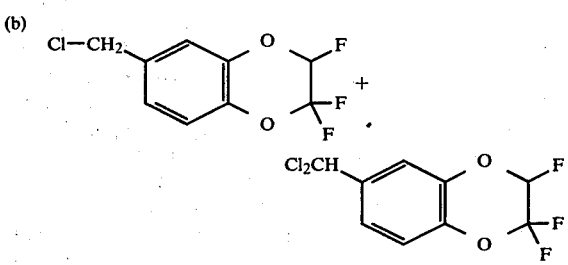

6-Chloromethyl-trifluorobenzodioxene and 6-dichloromethyl-trifluorobenzodioxene 1,065 g of 6-methyl-trifluorobenzodioxene were initially introduced at 120° C., while irradiating with UV light, and 440 g of chlorine were passed in. About 30 minutes after the introduction had ended, nitrogen was bubbled through and the mixture was then distilled over a packed column. After a small amount of first runnings, 760 g of 6-chloromethyl-trifluorobenzodioxene (boiling point: 114°–118° C./16 mm Hg) pass over. After intermediate runnings, 200 g of 6-dichloromethyl-trifluorobenzodioxene (boiling point 127° C./16 mm Hg) were also obtained.

(c)

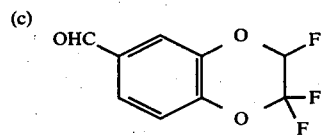

6-Formyl-trifluorobenzodioxene 190 g of urotropin were dissolved in 250 ml of water at 100° C. and 190 g of a mixture of 6-chloromethyl- and 6-dichloromethyl-trifluorobenzodioxene were added dropwise. After 1 hour a mixture of 200 ml of water and 200 ml of hydrochloric acid was added at 100° C. and the mixture was then stirred again at 100° C. for 2 hours.

The product was then driven over with steam and redistilled. Yield: 133 g of 6-formyl-trifluorobenzodioxene.

EXAMPLE 2

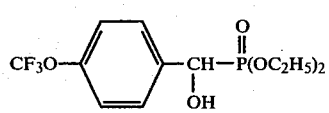

19 g (0.1 mol) of 4-trifluoromethoxy-benzaldehyde were passed into a mixture of 13.8 g (0.1 mol) of diethyl phosphite, 1 g of triethylamine and 1 ml of 20% strength sodium methylate solution at 50°-70° C. in the course of one hour, while cooling with water. The reaction batch was subsequently stirred at 60° C. After cooling, the batch was taken up in 50 ml of methylene chloride and rinsed several times with dilute hydrochloric acid and cold water. The organic layer was separated off and freed from solvent in vacuo. 26.2 g (79.9% of theory) of 4-trifluoro-methoxy-α-hydroxy-benzylphosphonic acid diethyl ester were obtained as a yellow, very viscous oil with the refractive index $n_D^{22}$: 1.4582.

The following compounds were prepared analogously:

| Intermediate | Formula |
|---|---|
| VI-2 | CH₃O—⟨⟩—CH(OH)—P(O)(OC₂H₅)₂ |
| Yield: 81.2% of theory | |
| VI-3 | (O-O-benzodioxole)—CH(OH)—P(O)(OC₂H₅)₂ |
| Yield: 85.5% of theory | |
| VI-4 | CF₃S—⟨⟩—CH(OH)—P(O)(OC₂H₅)₂ |
| Yield: 72.2% of theory | |
| VI-5 | C₂H₅O—⟨⟩—CH(OH)—P(O)(OC₂H₅)₂ |
| Yield: 83.6% of theory | |
| VI-6 | F₂C(O-)(O-)—⟨⟩—CH(OH)—P(O)(OC₂H₅)₂ |
| Yield: 78,6% of theory | |
| VI-7 | F₃C-CF(-O-)(-O-)—⟨⟩—CH(OH)—P(O)(OC₂H₅)₂ |
| Yield: 74.5% of theory | |

EXAMPLE 3

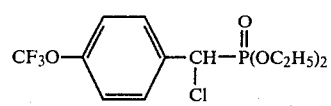

8.7 g (0.073 mol) of thionyl chloride were added to a mixture of 22.96 g (0.07 mol) of 4-trifluoromethoxy-α-hydroxy-benzylphosphonic acid diethyl ester, 70 ml of methylene chloride and 5.6 g (0.07 mol) of pyridine at 20°-40° C. in the course of about 1 hour, while cooling slightly with water. The reaction mixture was then heated to 50° C. for 3 hours and was subsequently stirred for 12 hours without further action of heat. The mixture was poured onto about 100 g of ice-water and the organic phase was separated off and dried. After distilling off the solvent, the residue was concentrated under 2 mm Hg and at 45° C. 18.7 g (77.1% of theory) of 4-trifluoromethoxy-α-chloro-benzyl-phosphonic acid diethyl ester were obtained as a yellow viscous oil with a refractive index of $n_D^{22}$: 1.4968.

The following compounds were obtained analogously:

| Intermediate | Formula |
|---|---|
| IV-2 | CH₃O—⟨⟩—CH(Cl)—P(O)(OC₂H₅)₂ |
| Yield: 91.2% of theory; refractive index: $n_D^{22}$: 1.5188 | |
| IV-3 | (O-O-benzodioxole)—CH(Cl)—P(O)(OC₂H₅)₂ |
| Yield: 75.2% of theory | |
| IV-4 | CF₃S—⟨⟩—CH(Cl)—P(O)(OC₂H₅)₂ |
| Yield: 66% of theory | |
| IV-5 | C₂H₅O—⟨⟩—CH(Cl)—P(O)(OC₂H₅)₂ |
| Yield: 88.7% of theory | |
| IV-6 | F₂C(O-)(O-)—⟨⟩—CH(Cl)—P(O)(OC₂H₅)₂ |
| IV-7 | F₃C-CF(-O-)(-O-)—⟨⟩—CH(Cl)—P(O)(OC₂H₅)₂ |
| Yield: 56.6% of theory | |

EXAMPLE 4

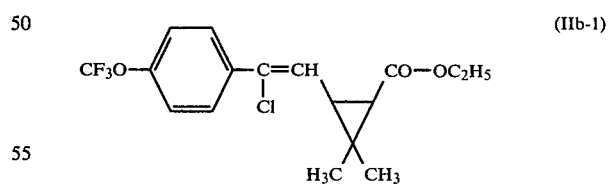

(IIb-1)

4.6 g (0.2 mol) of sodium were dissolved in portions in 100 ml of ethanol. When all the sodium had dissolved, 100 ml of tetrahydrofuran (anhydrous) were added and 69.3 g (0.2 mol) of 4-trifluoromethoxy-α-chlorobenzylphosphonic acid diethyl ester, dissolved in 50 ml of anhydrous tetrahydrofuran, were added dropwise at 0° C., while stirring. After stirring had been continued at 0°-5° C. for a further 2 hours, 34 g (0.2 mol) of cis/tran-2,2-dimethyl-3-formyl-cyclopropanecarboxylic acid ethyl ester, dissolved in 50 ml of anhydrous tetrahydrofuran, were added dropwise at 0° C., while stirring.

Stirring was then continued at 20°–25° C. for a further 12 hours. 600 ml of water were then added and the reaction mixture was extracted twice with 300 ml of methylene chloride each time. The organic phase was separated off and dried over magnesium sulphate, the solvent was distilled off under a waterpump vacuum and the residue was distilled in vacuo. 42.3 g (58.3% of theory) of 2,2-dimethyl-3-(2-chloro-2-(4-trifluoromethoxy-phenyl)-vinyl)-cyclopropanecarboxylic acid ethyl ester (cis, trans and E, Z isomer mixture) were obtained as a yellow oil with a boiling point of 160°–172° C./2 mm Hg.

The following compounds were obtained analogously:

| Intermediate | Formula |
|---|---|
| IIb-2 | CH₃O—⟨⟩—C(Cl)=CH—[cyclopropane(CH₃)₂]—CO—OC₂H₅ |

Yield: 68.8% of theory;
boiling point: 160–165° C./1 mm Hg

IIb-3: CF₃S—⟨⟩—C(Cl)=CH—[cyclopropane(CH₃)₂]—CO—OC₂H₅

Yield: 38.8% of theory;
boiling point: 160–170° C./1 mm Hg

IIb-4: methylenedioxy-⟨⟩—C(Cl)=CH—[cyclopropane(CH₃)₂]—CO—OC₂H₅

Yield: 69.4% of theory;
boiling point: 201–204° C./2 mm Hg

IIb-5: C₂H₅O—⟨⟩—C(Cl)=CH—[cyclopropane(CH₃)₂]—CO—OC₂H₅

IIb-6: F₂C(O)(O)—⟨⟩—C(Cl)=CH—[cyclopropane(CH₃)₂]—CO—OC₂H₅

Yield: 32% of theory, boiling point: 145–155° C./2mm Hg

IIb-7: CF₃—CF(O)(O)—⟨⟩—C(Cl)=CH—[cyclopropane(CH₃)₂]—CO—OC₂H₅

Yield: 40,2% of theory, boiling point: 155–175° C./2 mm Hg

EXAMPLE 5

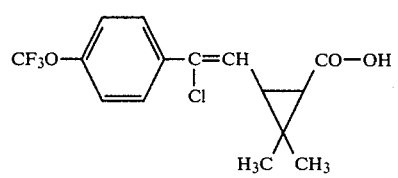

(II-1) CF₃O—⟨⟩—C(Cl)=CH—[cyclopropane(CH₃)₂]—CO—OH 30.8 g (0.085 mol) of 2,2-dimethyl-3-(2-chloro-2-(4-trifluoromethoxy-phenyl)-vinyl)-cyclopropanecarboxylic acid ethyl ester were dissolved in 100 ml of ethanol, a solution of 4 g (0.1 mol) of sodium hydroxide in 100 ml of water was then added and the mixture was heated to the reflux temperature for 4 hours, while stirring. The ethanol was then distilled off under a waterpump vacuum, the residue was taken up in 300 ml of warm water and the mixture was extracted once with 300 ml of methylene chloride. The aqueous phase was separated off, acidified with concentrated hydrochloric acid and then extracted with 2 times 300 ml of methylene chloride. The organic phase was then separated off and dried over magnesium sulphate and the solvent was distilled off under a waterpump vaccum. Last residues of solvent were removed by brief incipient distillation under 2 mm Hg at a bath temperature of 60° C. 19.4 g (68.3% of theory) of 2,2-dimethyl-3-(2-chloro-2-(4-trifluoromethoxy-phenyl)-vinyl)-cyclopropanecarboxylic acid (cis and trans, E and Z isomer mixture) were then obtained as a very viscous yellow oil. The structure was confirmed by the ¹H-NMR spectrum.

¹H-NMR (in CDCl₃/TMS): aromatic H: 7.65–6.9 δ (m/4H), vinyl H: 5.9–5.6 δ (m/1 H), cyclopropane H: 2.6–1.4 δ (m/2 H) and dimethyl H: 1.4–1.0 δ (m/6 H).

The following compounds were obtained analogously:

| Intermediate | Formula | Yield (% of theory) |
|---|---|---|
| II-2 | CH₃O—⟨⟩—C(Cl)=CH—[cyclopropane(CH₃)₂]—CO—OH | 76.8% |
| II-3 | CF₃S—⟨⟩—C(Cl)=CH—[cyclopropane(CH₃)₂]—CO—OH | — |
| II-4 | methylenedioxy-⟨⟩—C(Cl)=CH—[cyclopropane(CH₃)₂]—CO—OH | 74.4% |
| II-5 | C₂H₅O—⟨⟩—C(Cl)=CH—[cyclopropane(CH₃)₂]—CO—OH | 77.9% |
| II-6 | F₂C(O)(O)—⟨⟩—C(Cl)=CH—[cyclopropane(CH₃)₂]—COOH | 71,2% |
| II-7 | CF₃—CF(O)(O)—⟨⟩—C(Cl)=CH—[cyclopropane(CH₃)₂]—COOH | 76% |

EXAMPLE 6

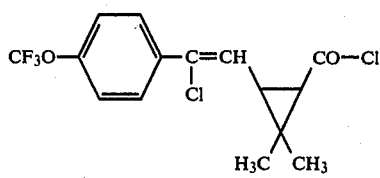
(IIa-1)

19.4 g (0.058 mol) of 2,2-dimethyl-3-(2-chloro-2-(4-trifluoromethoxy-phenyl)-vinyl)-cyclopropanecarboxylic acid were dissolved in 150 ml of carbon tetrachloride, and 15 g of thionyl chloride were slowly added dropwise at 25° C., while stirring. The mixture was then heated to the reflux temperature for 4 hours. After this reaction time, excess thionyl chloride and carbon tetrachloride were distilled off under a waterpump vacuum. Last residues of solvent were removed by brief incipient distillation under 2 mm Hg at a bath temperature of 60° C. 19.4 g (95% of theory) of 2,2-dimethyl-3-(2-chloro-2-(4-trifluoromethoxy-phenyl)-vinyl)-cyclopropanecarboxylic acid chloride were obtained as an oily liquid.

The following compounds were obtained analogously:

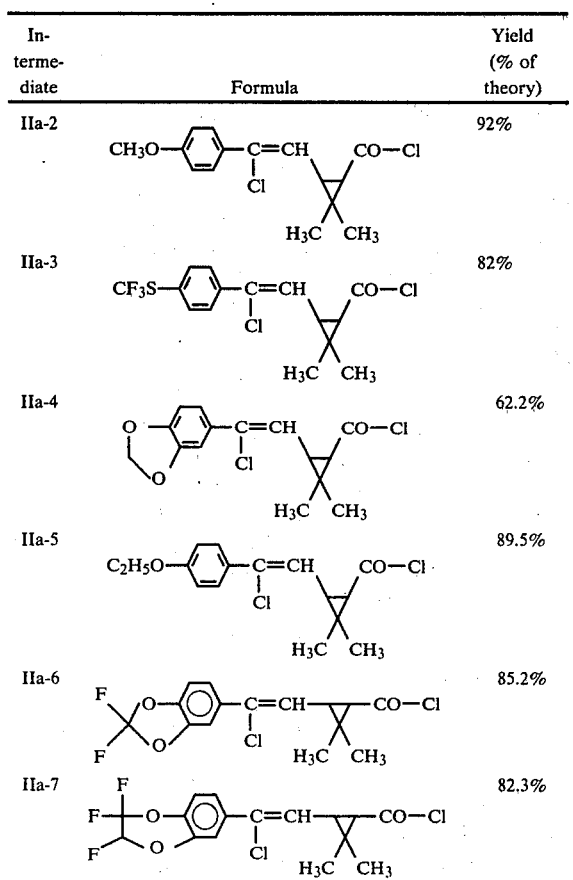

| Intermediate | Formula | Yield (% of theory) |
| --- | --- | --- |
| IIa-2 | | 92% |
| IIa-3 | | 82% |
| IIa-4 | | 62.2% |
| IIa-5 | | 89.5% |
| IIa-6 | | 85.2% |
| IIa-7 | | 82.3% |

The novel end products could be prepared as follows:

EXAMPLE 7

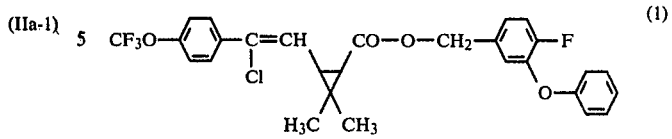
(1)

4.4 g (0.02 mol) of 3-phenoxy-4-fluoro-benzyl alcohol and 7.1 g (0.02 mol) of 2,2-dimethyl-3-(2-chloro-2-(4-trifluoromethoxy-phenyl)-vinyl)-cyclopropanecarboxylic acid chloride were dissolved in 100 ml of anhydrous toluene, and 2.5 g of pyridine, dissolved in 50 ml of anhydrous toluene, were added dropwise at 20°–25° C., while stirring. Stirring was then continued at 25°–35° C. for 3 hours. The reaction mixture was poured into 150 ml of water, to which 10 ml of concentrated hydrochloric acid were added, and the organic phase was separated off and washed again with 100 ml of water. The toluene phase was then dried over sodium sulphate and the solvent was distilled off under a water-pump vacuum. Last residues of solvent were removed by brief incipient distillation at a bath temperature of 60° C./1 mm Hg. 8.7 g (81.4% of theory) of 2,2-dimethyl-3-(2-chloro-2-(4-trifluoromethoxy-phenyl)-vinyl)-cyclopropanecarboxylic acid 4-fluoro-3-phenoxy-benzyl ester were obtained as a yellow oil with the refractive index $n_D^{23}$: 1.5443.

EXAMPLE 8

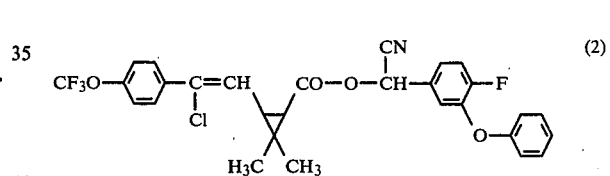
(2)

4.32 g (0.02 mol) of 3-phenoxy-4-fluoro-benzaldehyde and 7.1 g (0.02 mol) of 2,2-dimethyl-3-(2-chloro-2-(4-trifluoromethoxy-phenyl)-vinyl)-cyclopropanecarboxylic acid chloride were together added dropwise to a mixture of 1.6 g of sodium cyanide, 2.5 ml of water, 100 ml of n-hexane and 0.5 g of tetrabutylammonium bromide at 20°–25° C., while stirring, and the mixture was then stirred at 20°–25° C. for 4 hours. 300 ml of toluene were subsequently added, and the reaction mixture was extracted by shaking twice with 300 ml of water each time. The organic phase was separated off and dried over magnesium sulphate and the solvent was distilled off under a waterpump vacuum. Last residues of solvent were removed by brief incipient distillation at a bath temperature of 60° C./1 mm Hg. 7 g (62.6% of theory) of 2,2-dimethyl-3-(2-chloro-2-(4-trifluoromethoxy-phenyl)-vinyl)-cyclopropanecarboxylic acid 3-phenoxy-4-fluoro-α-cyano-benzyl ester were obtained as a viscous oil. The structure was confirmed by the $^1$H-NMR spectrum.

$^1$H-NMR spectrum (CDCl$_3$/TMS): aromatic H: 7.74–6.76δ(m/12H), benzyl H: 6.48–6.27δ(m/1H), vinyl H: 6.0–5.62δ(m/1H), cyclopropane H: 2.75–1.55δ(m/2H) and dimethyl H: 1.5–1.12δ(m/6H).

The following compounds 3–13 were obtained analogously to this and the preceding example:

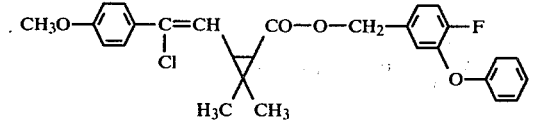

(3)

Yield: 84.5% of theory

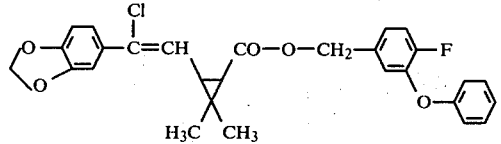

(4)

Yield: 82.9% of theory

¹H-NMR spectrum (CDCl₃/TMS): aromatic H: 7.65–6.7δ(m/11H), methylenedioxy H: 5.96δ(S/2H), vinyl H: 5.8–5.5δ(m/1H), benzyl H: 5.14–5.07δ(m/2H), cyclopropane H: 2.7–1.45δ(m/2H) and dimethyl H: 1.5–1.0δ(m/6H).

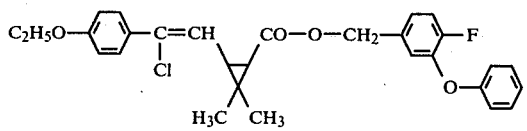

(5)

Yield: 79.3% of theory

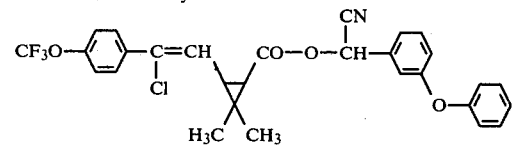

(6)

Yield: 72.5% of theory

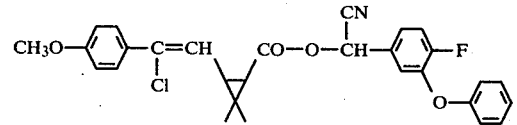

(7)

Yield: 74.6% of theory

¹H-NMR spectrum (CDCl₃/TMS): aromatic H: 7.6–6.7δ(m/1H), benzyl H: 6.4–6.22δ(m/1H), vinyl H: 5.83–5.5δ(m/1H), methoxy H: 3.78δ(S/3H), cyclopropane H: 2.7–1.45δ(m/2H) and dimethyl H: 1.4–1.1δ(m/6H).

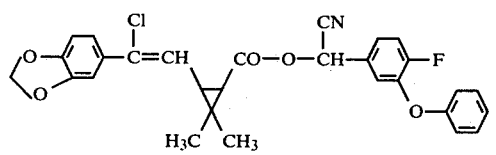

(8)

¹H-NMR spectrum (CDCl₃/TMS): aromatic H: 7.67–6.7δ(m/11H), benzyl H: 6.43–6.24δ(m/1H), methylenedioxy H: 5.95δ(S/2H), vinyl H: 5.8–5.5δ(m/1H), cyclopropane H: 2.74–1.48δ(m/2H) and dimethyl H: 1.4–0.9δ(m/6H).

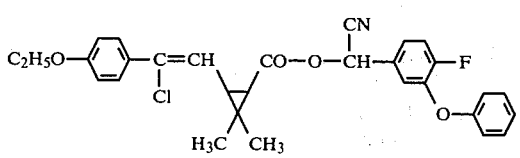

(9)

Yield: 72.8% of theory

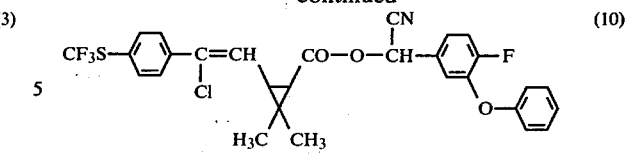

(10)

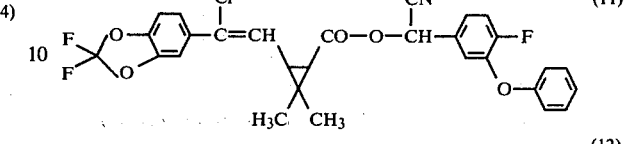

(11)

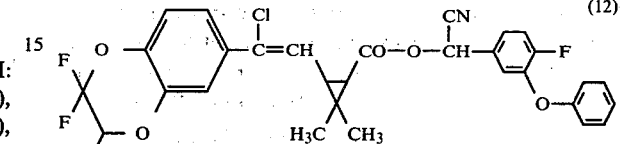

(12)

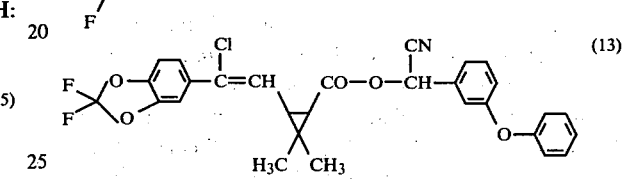

(13)

The pesticidal activity of the compounds of this invention is illustrated by the following examples wherein the compounds according to the present invention are each identified by the number (given in brackets) from Examples 7 and 8:

EXAMPLE 9

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound and were infested with mustard beetle larvae (*Phaedon cochleariae*), as long as the leaves were still wet.

After the specified periods of time, the degree of destruction was determined in %: 100% meant that all of the beetle larvae had been killed whereas 0% meant that none of the beetle larvae had been killed.

In this test, for example, the following compounds showed a superior activity compared to the prior art: (1), (2), (6), (7) and (8).

EXAMPLE 10

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus*

*urticae*) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (7), (1) and (2).

EXAMPLE 11

Test with *Boophilus microplus* resistant
Solvent: 35 parts by weight of ethylene glycol monoethyl ether, 35 parts by weight of nonyl phenol polyglycol ether To produce a suitable preparation of active compound, three parts by weight of active compound were mixed with seven parts by weight of the solvent mixture indicated above, and the concentrate thus obtained was diluted with water to the desired concentration.

10 adult specimens of *Boophilus microplus* res. were immersed for 1 minute in the active compound preparation to be tested. After transfer to plastic beakers and storage in a climatically controlled chamber, the degree of destruction was determined.

In this test, for example, the following compounds showed a superior activity compared to the prior art (7), (3), (2), (1), (4) and (8).

It will be appreciated that the instant specification and examples are set forth by way of illustration and not limitation, and that various modifications and changes may be made without departing from the spirit and scope of the present invention.

What is claimed is:

1. A substituted styrylcyclopropanecarboxylic acid ester of the formula

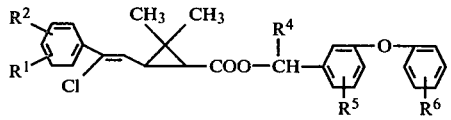

in which
R$^1$ represents C$_1$–C$_2$-fluoroalkoxy, C$_1$–C$_2$-chlorofluoroalkoxy or C$_1$–C$_2$-fluoroalkylthio and
R$^2$ represents hydrogen or methoxy, or
R$^1$ and R$^2$ together represent C$_1$–C$_2$-fluoroalkylenedioxy,
R$^4$ represents hydrogen, cyano or ethynyl and
R$^5$ and R$^6$ independently represent hydrogen or fluorine.

2. A compound according to claim 1, wherein such compound is 2,2-dimethyl-3-(2-chloro-2-(4-trifluoromethoxy-phenyl)-vinyl)-cyclopropanecarboxylic acid 4-fluoro-3-phenoxy-benzyl ester of the formula

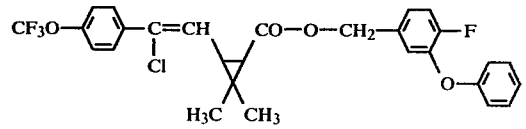

3. A compound according to claim 1, wherein such compound is 2,2-dimethyl-3-(2-chloro-2-(4-trifluoromethoxy-phenyl)-vinyl)-cyclopropanecarboxylic acid 3-phenoxy-4-fluoro-α-cyano-benzyl ester of the formula

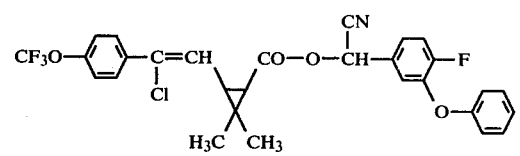

4. A compound according to claim 1, wherein such compound is 2,2-dimethyl-3-(2-chloro-2-(4-trifluoromethoxy-phenyl)-vinyl)-cyclopropanecarboxylic acid 3-phenoxy-α-cyano-benzyl ester of the formula

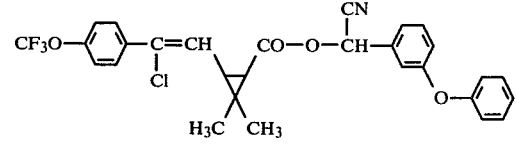

5. An arthropodicidal composition containing as active ingredient an arthropodicidally effective amount of a compound according to claim 1 in admixture with a diluent.

6. A method of combating arthropods which comprises applying to the arthropods, or to a habitat thereof, an arthropodicidally effective amount of a compound according to claim 1.

7. The method according to claim 6, wherein such compound is
2,2-dimethyl-3-(2-chloro-2-(4-trifluoromethoxyphenyl)-vinyl)-cyclopropanecarboxylic acid 4-fluoro-3-phenoxy-benzyl ester,
2,2-dimethyl-3-(2-chloro-2-(4-trifluoromethoxyphenyl)-vinyl)-cyclopropanecarboxylic acid 3-phenoxy-4-fluoro-α-cyano-benzyl ester, and
2,2-dimethyl-3-(2-chloro-2-(4-trifluoromethoxyphenyl)-vinyl)-cyclopropanecarboxylic acid 3-phenoxy-α-cyano-benzyl ester.

* * * * *